(12) United States Patent
Nishida

(10) Patent No.: US 9,101,409 B2
(45) Date of Patent: Aug. 11, 2015

(54) INTER-SPINOUS PROCESS IMPLANT

(75) Inventor: Kotaro Nishida, Kobe (JP)

(73) Assignee: National University Corporation Kobe University, Hyogo (JP)

( * ) Notice: Subject to any disclaimer, the term of this patent is extended or adjusted under 35 U.S.C. 154(b) by 364 days.

(21) Appl. No.: 13/583,088

(22) PCT Filed: Feb. 11, 2011

(86) PCT No.: PCT/JP2011/000781
§ 371 (c)(1),
(2), (4) Date: Sep. 6, 2012

(87) PCT Pub. No.: WO2011/111301
PCT Pub. Date: Sep. 15, 2011

(65) Prior Publication Data
US 2012/0330360 A1    Dec. 27, 2012

(30) Foreign Application Priority Data

Mar. 9, 2010 (JP) .............................. JP2010-052414

(51) Int. Cl.
*A61F 2/44* (2006.01)
*A61B 17/70* (2006.01)
*A61B 17/16* (2006.01)

(52) U.S. Cl.
CPC .......... *A61B 17/7062* (2013.01); *A61B 17/1655* (2013.01); *A61F 2/4405* (2013.01)

(58) Field of Classification Search
CPC ..... A61F 2/4465; A61F 2/4405; A61F 2/442; A61B 17/7062
USPC ...................................................... 623/17.16
See application file for complete search history.

(56) References Cited

U.S. PATENT DOCUMENTS

| 4,537,185 | A | * | 8/1985 | Stednitz | ......................... 606/304 |
| 5,458,638 | A | * | 10/1995 | Kuslich et al. | ............. 623/17.11 |

(Continued)

FOREIGN PATENT DOCUMENTS

| JP | 2009-195313 A | 9/2009 |
| WO | 2004/105656 A1 | 12/2004 |

(Continued)

OTHER PUBLICATIONS

International Search Report mailed on Mar. 8, 2011 for the corresponding International patent application No. PCT/JP2011/000781 (English translation attached).

*Primary Examiner* — Eduardo C Robert
*Assistant Examiner* — Stuart S Bray
(74) *Attorney, Agent, or Firm* — Posz Law Group, PLC

(57) ABSTRACT

An inter-spinous implant includes an approximately conical screw portion, further having a screw thread, which can be screwed between spinous processes; a head portion of an approximate inverted frustum shape of the same axis as the screw portion; a spacer portion that is formed between the screw portion and the head portion in the axial direction; and a through hole that passes through the axial center of the screw portion, the spacer portion, and the head portion. At least one slit is formed in the major axial direction of the total shape of the implant, having at least one-third the length of the total length of the major axial direction, the depth whereof reaching the through hole. Disposing the slit in the major axial direction of the implant proper imparts flexibility and elasticity to the implant overall, simplifies the installation and insertion of the implant.

8 Claims, 13 Drawing Sheets

(56) References Cited

U.S. PATENT DOCUMENTS

| | | | |
|---|---|---|---|
| 6,093,207 A * | 7/2000 | Pisharodi | 623/17.16 |
| 6,096,081 A * | 8/2000 | Grivas et al. | 623/17.11 |
| 6,500,205 B1 * | 12/2002 | Michelson | 623/17.16 |
| 6,562,039 B1 * | 5/2003 | Wang et al. | 606/247 |
| 6,562,041 B1 * | 5/2003 | Yonemura et al. | 606/279 |
| 6,648,916 B1 * | 11/2003 | McKay | 623/17.11 |
| 7,048,765 B1 * | 5/2006 | Grooms et al. | 623/17.16 |
| 7,128,760 B2 * | 10/2006 | Michelson | 623/17.16 |
| 7,273,498 B2 * | 9/2007 | Bianchi et al. | 623/17.16 |
| 7,410,501 B2 * | 8/2008 | Michelson | 623/17.15 |
| 7,655,046 B2 * | 2/2010 | Dryer et al. | 623/17.15 |
| 7,674,295 B2 * | 3/2010 | Eckman | 623/17.11 |
| 7,828,848 B2 * | 11/2010 | Chauvin et al. | 623/17.16 |
| 7,963,991 B2 * | 6/2011 | Conner et al. | 623/17.11 |
| 8,075,621 B2 * | 12/2011 | Michelson | 623/17.15 |
| 8,142,479 B2 * | 3/2012 | Hess | 606/248 |
| 8,262,736 B2 * | 9/2012 | Michelson | 623/17.16 |
| 8,277,487 B2 * | 10/2012 | Nishida | 606/249 |
| 8,277,510 B2 * | 10/2012 | Kleiner | 623/17.16 |
| 8,403,990 B2 * | 3/2013 | Dryer et al. | 623/17.15 |
| 8,435,299 B2 * | 5/2013 | Chauvin et al. | 623/17.16 |
| 8,486,120 B2 * | 7/2013 | Shimko | 606/303 |
| 8,702,757 B2 * | 4/2014 | Thommen et al. | 606/249 |
| 8,790,407 B2 * | 7/2014 | Chauvin et al. | 623/17.16 |
| 2001/0016743 A1 * | 8/2001 | Zucherman et al. | 606/61 |
| 2002/0040243 A1 * | 4/2002 | Attali et al. | 623/17.16 |
| 2002/0116066 A1 * | 8/2002 | Chauvin et al. | 623/17.16 |
| 2002/0143401 A1 * | 10/2002 | Michelson | 623/17.16 |
| 2003/0078668 A1 * | 4/2003 | Michelson | 623/17.16 |
| 2003/0100949 A1 * | 5/2003 | Michelson | 623/17.11 |
| 2004/0064058 A1 * | 4/2004 | McKay | 600/506 |
| 2004/0210311 A1 * | 10/2004 | Lange et al. | 623/17.11 |
| 2004/0210313 A1 * | 10/2004 | Michelson | 623/17.11 |
| 2005/0038513 A1 * | 2/2005 | Michelson | 623/17.11 |
| 2005/0065608 A1 * | 3/2005 | Michelson | 623/17.11 |
| 2005/0113929 A1 * | 5/2005 | Cragg et al. | 623/17.16 |
| 2005/0165398 A1 * | 7/2005 | Reiley | 606/61 |
| 2006/0184248 A1 * | 8/2006 | Edidin et al. | 623/17.11 |
| 2006/0241774 A1 * | 10/2006 | Attali et al. | 623/17.16 |
| 2006/0265066 A1 * | 11/2006 | Zucherman et al. | 623/17.11 |
| 2007/0149972 A1 | 6/2007 | Nakajima et al. | |
| 2008/0027438 A1 * | 1/2008 | Abdou | 606/61 |
| 2008/0071377 A1 * | 3/2008 | Conner et al. | 623/17.16 |
| 2008/0147193 A1 * | 6/2008 | Matthis et al. | 623/17.16 |
| 2008/0249629 A1 * | 10/2008 | Eckman | 623/17.16 |
| 2009/0093885 A1 * | 4/2009 | Levieux et al. | 623/17.16 |
| 2009/0099603 A1 * | 4/2009 | Nishida | 606/249 |
| 2009/0125066 A1 * | 5/2009 | Kraus et al. | 606/279 |
| 2009/0149959 A1 * | 6/2009 | Conner et al. | 623/17.16 |
| 2009/0171461 A1 * | 7/2009 | Conner et al. | 623/17.11 |
| 2009/0270989 A1 * | 10/2009 | Conner et al. | 623/17.16 |
| 2010/0057208 A1 * | 3/2010 | Dryer et al. | 623/17.16 |
| 2010/0191287 A1 * | 7/2010 | Bucci | 606/249 |
| 2010/0234889 A1 * | 9/2010 | Hess | 606/249 |
| 2010/0262243 A1 * | 10/2010 | Zucherman et al. | 623/17.12 |
| 2011/0009972 A1 * | 1/2011 | Chauvin et al. | 623/17.16 |
| 2012/0004729 A1 * | 1/2012 | Zipnick | 623/17.16 |
| 2012/0203346 A1 * | 8/2012 | Kraus | 623/17.16 |
| 2012/0330360 A1 * | 12/2012 | Nishida | 606/249 |
| 2013/0204303 A1 * | 8/2013 | Guizzardi et al. | 606/263 |
| 2013/0310940 A1 * | 11/2013 | Chauvin et al. | 623/17.16 |
| 2013/0310941 A1 * | 11/2013 | Chauvin et al. | 623/17.16 |
| 2013/0310943 A1 * | 11/2013 | McCormack et al. | 623/17.16 |

FOREIGN PATENT DOCUMENTS

| | | |
|---|---|---|
| WO | 2007/018114 A1 | 2/2007 |
| WO | WO 2007018114 A1 * | 2/2007 |

* cited by examiner (a)

The spinal canal is stenosed.

(b)

(c) C-C' cross sectional view

INTER-SPINOUS PROCESS IMPLANT

CROSS REFERENCE TO RELATED APPLICATIONS

This application is a U.S. national stage application of PCT/JP2011/000781 filed on Feb. 11, 2011, and claims priority to, and incorporates by reference, Japanese Patent Application No. 2010-052414 filed on Mar. 9, 2010.

The present invention relates to a minimally-invasive implant for the purpose of opening and enlargement of a processus spinosus interspace, and particularly an implant stationed in a processus spinosus interspace for the purpose of opening and enlarging the processus spinosus interspace in lumbar vertebra.

BACKGROUND

The spinal canal is a cylindrical space in a vertical direction located in the center of a backbone (corpus vertebrae), and a spinal cord and cauda quine (nerve) are housed therein and protected firmly. Spinal canal stenosis where this spinal canal is stenosed due to various causes such as deformation of a bone, a cartilage or a ligament to press the nerve therein has become a major social problem as the number of patients has exceeded those suffering from a herniated disc.

In particular, lumbar spinal canal stenosis refers to a state where the deformation and thickening of lumbar vertebra and intervertebral joints as well as deformation and bulging of the intervertebral disc which is cartilage tissue, or hypertrophy of a ligament occurs and these make the spinal canal narrow to apply pressure or squeeze the nerves and blood vessels.

As conservative therapeutic methods which improve symptoms in daily life, physical therapies such as drug therapy of administering a drug which is a vasodilator drug or increases blood flow to a nerve root or a periphery of the cauda quine, an epidural block method, a radicular block method, an orthosis therapy of wearing a lumbar vertebra bending position corset to keep the lumbar portion at rest at the bending position, and an ultrasonic therapy and a hot pack therapy for improving pain relief, muscular spasticity and blood circulation are available.

When the conservative therapy is ineffective and severe neurological disorder and intermittent claudication sustain, a surgical therapy is performed. As a conventional surgical therapy, neurological decompression procedures such as laminectomy and expanded fenestration have been performed.

In the laminectomy and expanded fenestration, surgical invasion is applied to the patient to restore the lumbar vertebra stenosis site, and thus it is necessary to give general anesthesia to the patient. In this procedure, the patient is likely to be exposed to the risk of hemorrhaging and serious complications, and hospitalization for several days to several weeks is required for a patient after the operation. Therefore, this procedure heavily burdens the patient, and particularly when the patient is elderly, the symptom is sometimes further worsened.

In recent years, it has been reported that by stationing an interspinous process spacer in a minor surgical method, the effect of local lumbar anteflexion is obtained and satisfactory results are obtained (Patent Document 1,2).

Such a minimally invasive procedure can be performed under a local anesthesia. Thus, a shorter period is needed for recovery, there is almost no hemorrhaging, the risk of serious complications is reduced and therapeutic cost required for the patient is less. Therefore, it has been desired that spinal canal stenosis can be treated using the minimally invasive procedure.

The present inventor has already proposed an interspinous implant for the purpose of realizing a more minimally invasive therapeutic method for spinal canal stenosis, while allowing simply stationing an interspinous spacer without the need for a large skin incision and also without the need for detaching the paraspinal muscle from the spine (Patent Document 3).

It is an unprecedented implant with an advantage such that it can be inserted obliquely instead of exactly from the side surface on the assumption that the spacer is inserted from processus spinosus side. It is therefore possible to insert the implant in the shortest linear route from the outside of the body and further minimize invasion to surrounding tissues.

The proposed interspinous implant includes a substantially conoid screw region to be screwed into a processus spinosus interspace, a spacer region formed in a longitudinal direction of the screw region, a head region which is interlockable with a tool arbitrarily or attachable to a coupling member arbitrarily, and a through-hole in an axial center of the screw region, the spacer region and the head region.

According to the proposed interspinous implant, a processus spinosus interspace can be enlarged smoothly while the screw region is screwed and inserted in the processus spinosus interspace, and the spacer region is pinched by passing the screw region through the processus spinosus interspace. Thus, eventually, the space between adjacent processus spinosus can be enlarged and fixed (a predetermined distance can be maintained) and it also becomes possible to insert and station the interspinous implant percutaneously even under local anesthesia, whereby a minimally invasive operation can be realized.

Moreover, the proposed interspinous implant far exceeds the prior and existing spacer device in that the interspinous implant can be stationed without the need for detaching the paraspinal muscle from the spine, and an early effect after operation can be anticipated with the possibility of an outpatient, making it possible to further reduce temporal, physical and financial burdens on the patient.

[Patent document1]U.S. Patent Publication No. 2005/0165398

[Patent document 2] WO 2004/105656

[Patent document 3] WO 2007/018114

In the above implant stationed in a processus spinosus interspace in lumbar vertebra, presumably a considerable stress is applied to the processus spinosus which comes in contact with the implant. Such a stress may possibly result in bone destruction of the processus spinosus.

The present invention aims at reducing a dynamic stress excessively applied to processus spinosus resulting from insertion of an interspinous implant and also providing an interspinous implant which can be expected to exhibit effects of inserting the implant for a long period of time.

In order to solve the above problems, the interspinous implant according to the present invention comprises:
1) a substantially conoid screw region having screw threads to be screwable into a processus spinosus interspace;
2) a head region of a substantially inverse truncated conoid shape formed coaxially with the screw region;
3) a spacer region formed in an axial direction between the screw region and the head region; and
4) a through-hole penetrating an axial center of the screw region, the spacer region and the head region, wherein
   at least one slit or groove is formed in a long axis direction of the entire shape of the implant by occupying more than one third of the full length of the implant in the long axis direction and the slit or groove is deep enough to reach the through-hole.

Owing to at least one slit or groove formed in a long axis direction of the entire shape of the implant with a length which is more than one third of the full length of the implant in the long axis direction and a depth reaching the through-hole, the entire implant is allowed to bend and given elasticity in a direction vertical to the long axis direction. Due to the flexibility and elasticity, it becomes possible to reduce a dynamic stress excessively applied to processus spinosus resulting from insertion of the implant. Accordingly, effects of inserting the implant for a long period of time can be anticipated.

Here, the above slit or groove is preferably formed continuously through the screw region, the spacer region and the head region.

By forming the slit or groove in the screw region, it becomes possible to reduce a dynamic stress applied to processus spinosus when the implant is inserted. Also, by forming the slit or groove in the spacer region, it becomes possible to reduce a dynamic stress applied to processus spinosus resulting from the presence of the implant in the processus spinosus interspace for a long period of time. Further, by forming the slit or groove in the head region, it becomes possible to reduce a dynamic stress applied to processus spinosus when the implant is removed from the processus spinosus interspace.

Moreover, in the event of inserting the implant, owing to a configuration such that the screw region is formed into a substantially conoid shape and a joint portion of the head region to be joined to a driver at insertion is allowed to move to some extent, when the implant is inserted to some extent, the tip end region of the implant comes in contact with an opposed intervertebral joint or other tissues and proceeds therealong while changing its direction toward where there is less resistance, resulting in the implant being fitted in appropriate alignment as a whole and stabilized (referred to as three-dimensional self-alignment function of the implant hereinafter).

More specifically, it is preferable that the slit or groove is formed continuously to cover more than half of a dimension of the substantially conoid shape of the screw region in the axial direction, a dimension of the spacer region in the axial direction and more than half of a dimension of the substantially inverse truncated conoid shape of the head region in the axial direction.

The present implant is made of the substantially conoid screw region, the head region of a substantially inverse truncated conoid shape and the spacer region formed in the axial direction between the screw region and the head region. Therefore, if the slit or groove is formed continuously to cover more than half of a dimension of the substantially conoid shape of the screw region in the axial direction, a dimension of the spacer region in the axial direction and more than half of a dimension of the substantially inverse truncated conoid shape of the head region in the axial direction, the slit or groove will have a length of about half to two thirds of the full length of the implant in the axial direction.

As a result, flexibility and elasticity are improved in the entire implant with better performance of the three-dimensional self-alignment function of the implant and it becomes possible to reduce a dynamic stress excessively applied to processus spinosus resulting from insertion of the implant.

Here, the reason why the slit or groove is to have a partial length of the full length of the screw region and the head region in the axial direction is to ensure the strength of the entire implant.

In addition, even if the above slit or groove is formed only in the spacer region, it can be preferably used.

As stated above, by forming the slit or groove in the spacer region, it becomes possible to reduce a dynamic stress applied to processus spinosus resulting from the presence of the implant interspace for a long period of time. Even with the slit or groove which is formed only in the spacer region, effects of inserting the implant for a longer period of time can be anticipated.

Here, it is preferable that a width of the slit or groove falls in a range of 0.5 to 1.5 mm. The present implant is an interspinous implant for the purpose of performing a minimally invasive operation for lumbar spinal canal stenosis and the implant itself has a diameter of about 10 to 15 mm. Therefore, the width of the slit or groove is adjusted to a range of depth allowing exhibition of flexibility and elasticity of the implant itself and depth which does not impair the strength of the implant itself.

Moreover, the entire shape of the implant is preferably a spindle shape. By forming a three-dimensional shape of the entire implant into a spindle shape and giving some play of about 30 degrees to the driver joint part in the head region or allowing usage of a multi-axial driver, it is made easier to exhibit the three-dimensional self-alignment function of the implant at insertion and extraction of the implant.

Here, a cross section of the spacer region is preferably circular, elliptical, substantially triangular, substantially rectangular or polygonal with a plurality of slits or grooves arranged therein at even intervals.

By arranging a plurality of slits or grooves at even intervals, the strength of the implant itself can be retained and it is possible to reduce a risk of processus spinosus coming in contact with the edge of the slits or grooves.

For instance, if a cross section of the spacer region is circular or elliptical, two slits or grooves are arranged at 180° intervals (diagonally) to be seen from the axial direction, three slits or grooves are arranged at 120° intervals to be seen from the axial direction, and four slits or grooves are arranged at 90° intervals to be seen from the axial direction.

If a cross section of the spacer region is substantially triangular, in order to reduce a risk of processus spinosus coming in contact with the edge of slits or grooves, three slits or grooves are arranged in the vicinity of the center of three flat side surfaces. As a result, three slits or grooves are placed at even intervals.

Similarly, if a cross section of the spacer region is substantially rectangular, in order to reduce a risk of processus spinosus coming in contact with the edge of slits or grooves, four slits or grooves are arranged in the vicinity of the center of four flat side surfaces. As a result, four slits or grooves are placed at even intervals.

Explained next will be a tap for interspinous implant for use in inserting the interspinous implant according to the present invention into a processus spinosus interspace.

The tap for interspinous implant according to the present invention is provided with: 1) a tip end region which is formed into a conoid shape with a more acute angle than the conus of the screw region of the interspinous implant and has screw threads occupying one third to one fifth of the generatrix from the tip end of the conoid shape; 2) an axial center region extending in an axial direction of the tip end region, whose diameter is less than a diameter of the skirts of the tip end region and whose dimension in a longitudinal direction exceeds a length from an incision site to a processus spinosus interspace; 3) a grip region fitted in the axial center region; and 4) a through-hole linearly penetrating a space from the tip end region to the end of the grip region bypassing through the axial center region.

The tap for interspinous implant according to the present invention is used in a pretreatment to allow smooth insertion of the interspinous implant from a small skin incision. The tip end region of the tap for interspinous implant is formed into a more distinct conoid shape than the interspinous implant and screw threads are created therein by occupying one third to one fifth of the generatrix from the tip end of the conoid shape. This tap is used to create a passage in a processus spinosus interspace to some extent so that an interval of the processus spinosus is opened and enlarged slightly. By using the tap for interspinous implant according to the present invention in a pretreatment, there is an advantage that the screw region of the interspinous implant in which similar screw threads have been created can be inserted more easily. The screw threads are created only up to halfway in a range of one third to one fifth of the generatrix from the tip end of the conoid shape, so that opening and enlarging a processus spinosus interspace more than necessary is prevented.

A guide pin is passed through the through-hole which penetrates a space from the tip end region to the end of the grip region by passing through the axial center region so that the tap for interspinous implant can be inserted into the body along the guide pin, whereby the tip end region of the tap can be guided accurately into a processus spinosus interspace.

Using the tap for interspinous implant according to the present invention also has an advantage that the magnitude of resistance felt by the operator on the hand when the tap is inserted can be used as a reference to select an appropriate size of the interspinous implant for the patient.

SUMMARY

The interspinous implant according to the present invention has an advantage that, by providing a slit or groove in the long axis direction of the implant itself with a depth reaching the through hole so as to allow the entire implant to bend with elasticity, placement and insertion of the implant is simplified and effects of opening and enlarging a processus spinosus interspace can be maintained for a long period of time without causing an excessive stress applied to the processus spinosus which comes in contact with the implant.

Owing to the above advantages, bone destruction of processus spinosus can be reduced.

Next, the tap for interspinous implant according to the present invention has an advantage that the screw region serving as an introduction part of the implant can be inserted more easily. In addition, because screw threads are created only up to halfway through the conoid shape of the tip end region in the tap for interspinous implant according to the present invention, opening and enlarging of a processus spinosus interspace more than necessary can be prevented and bone destruction of processus spinosus can be reduced.

Further, creating screw threads only up to halfway in the tap has an advantage of not only preventing bone destruction of processus spinosus but also preventing destruction of bone tissues and nerve tissues as typified by an opposed intervertebral joint.

DETAILED DESCRIPTION

The present embodiment explained below is to be considered in all respects without being limited, and all changes that occur within the meanings of claims and the equivalent scope are intended to be included therein.

Embodiment 1

An interspinous implant according to Embodiment 1 will be explained by using FIGS. 1 to 12.

Figure 1:
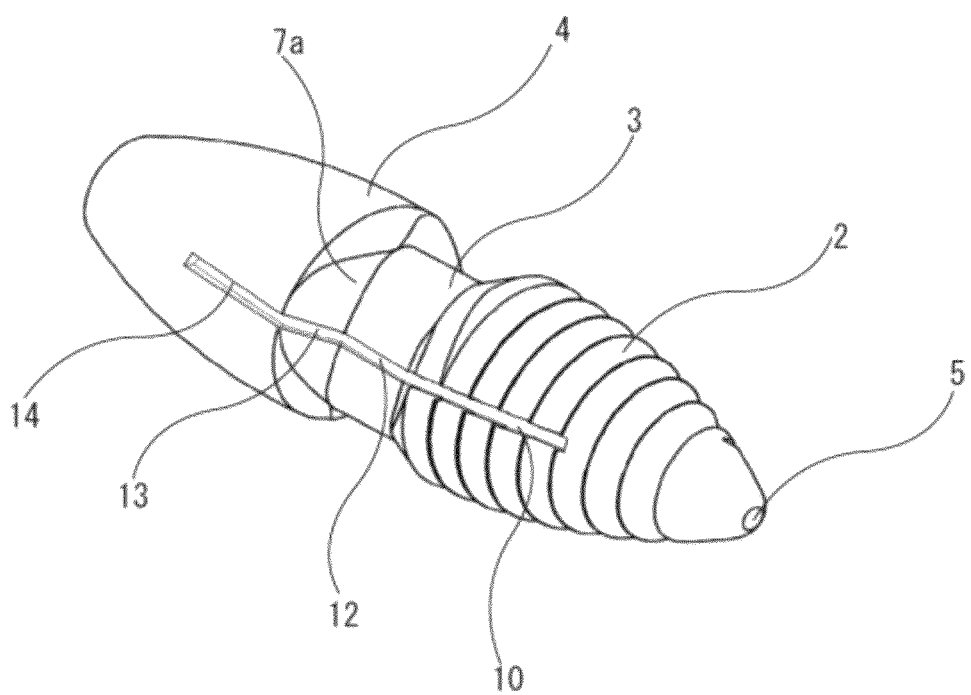
FIG. 1 shows an external perspective view of the interspinous implant in Embodiment 1 to be seen from a screw region.
Figure 2:
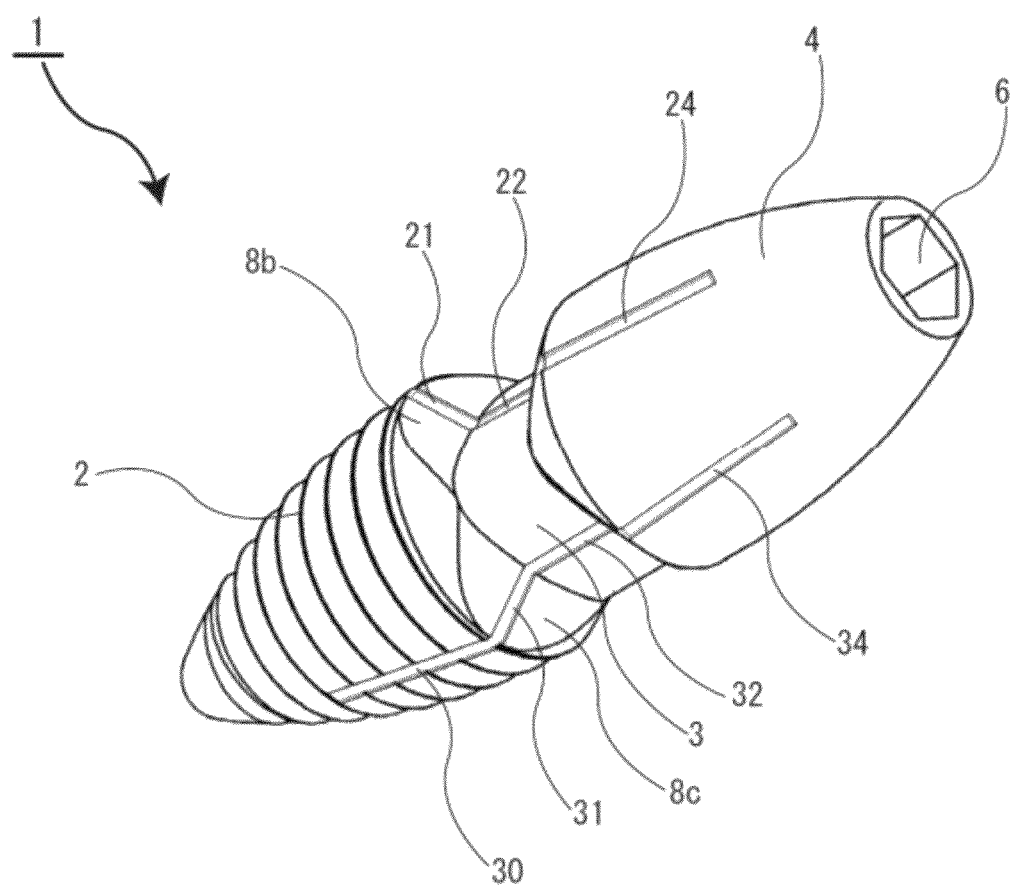
FIG. 2 shows an external perspective view of the interspinous implant to be seen from a head region.
Figure 3:
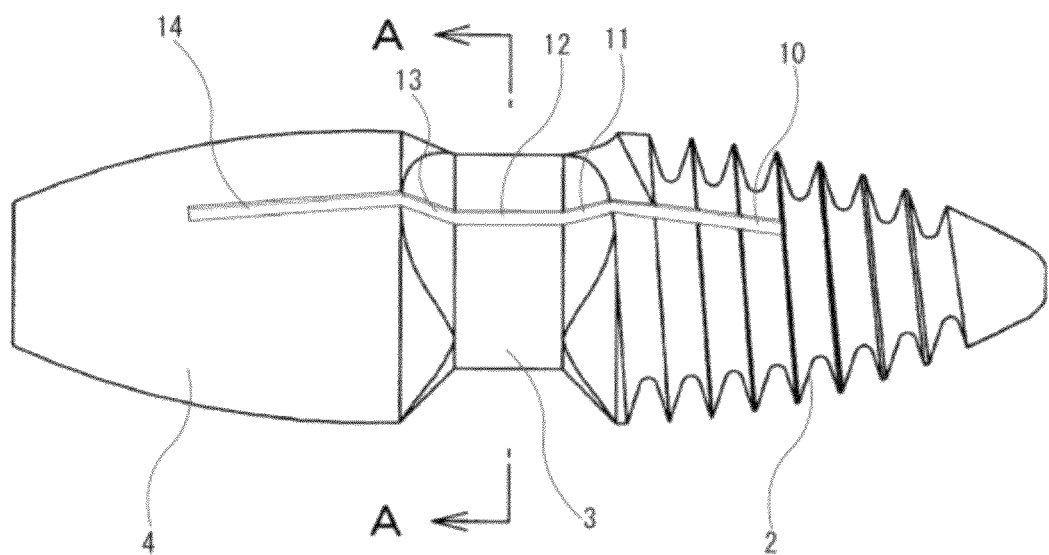
FIG. 3 shows a front view of the interspinous implant (long axis direction is disposed horizontally).
Figure 4:
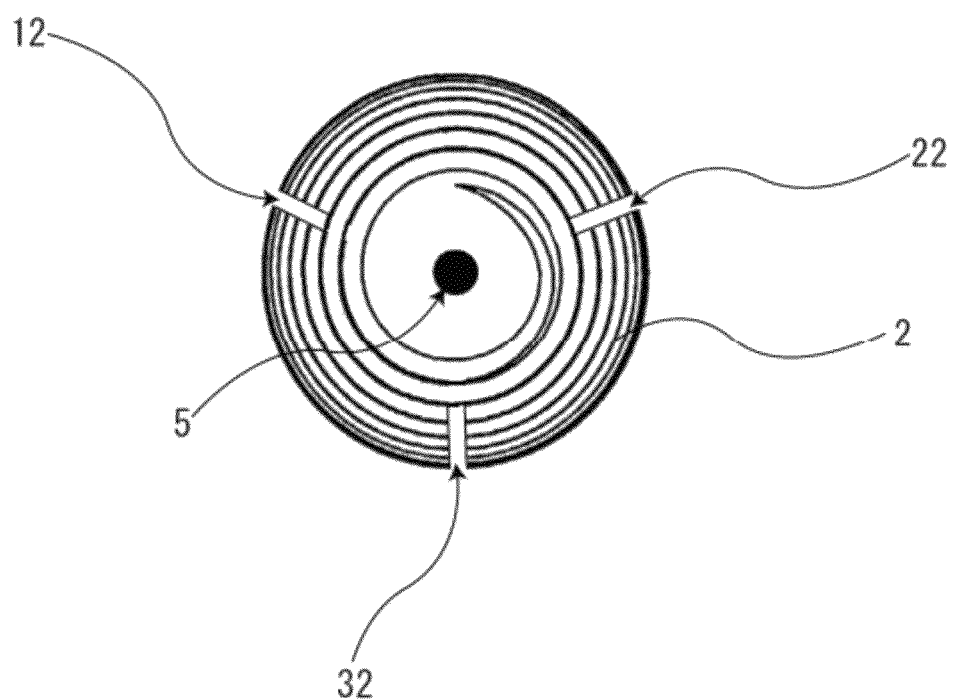
FIG. 4 shows a right side view of the interspinous implant (to be seen from the screw region).
Figure 5:
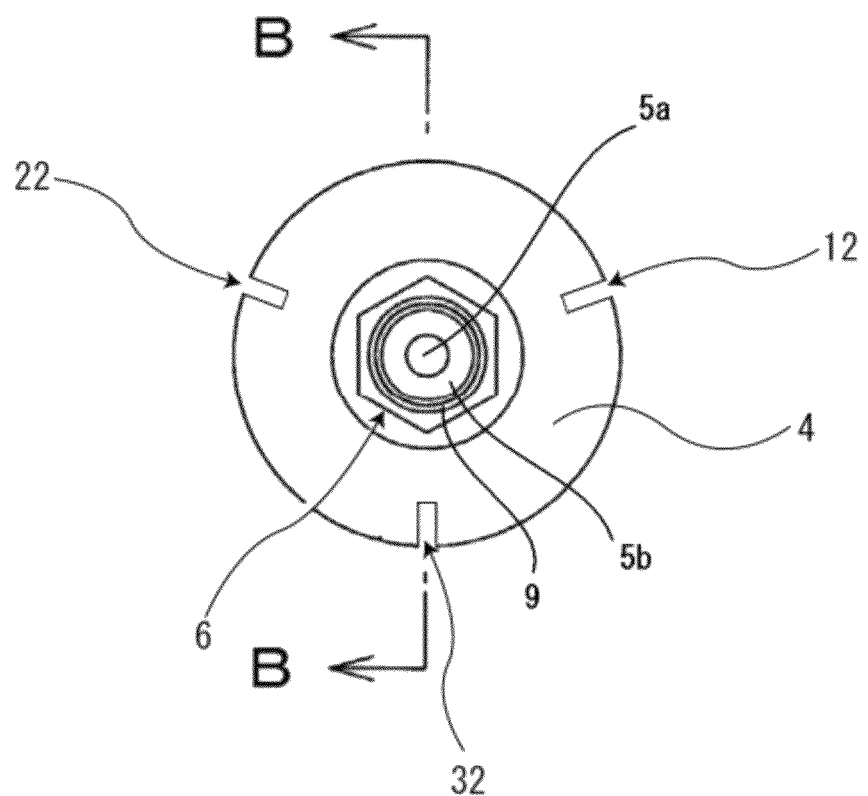
FIG. 5 shows a left side view of the interspinous implant (to be seen from the head region).
Figure 6:
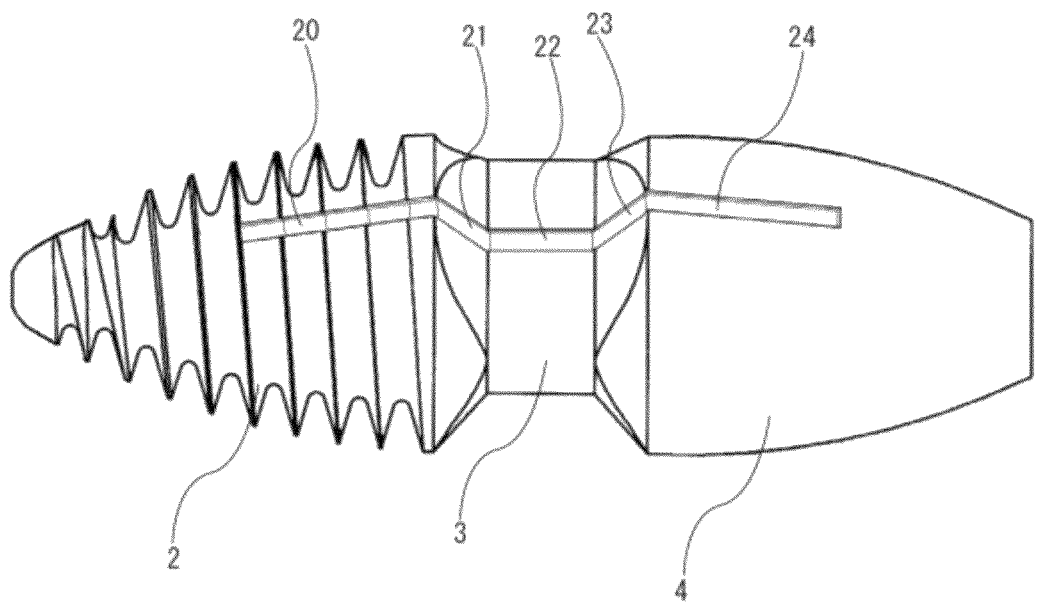
FIG. 6 shows a rear view of the interspinous implant.
Figure 7:
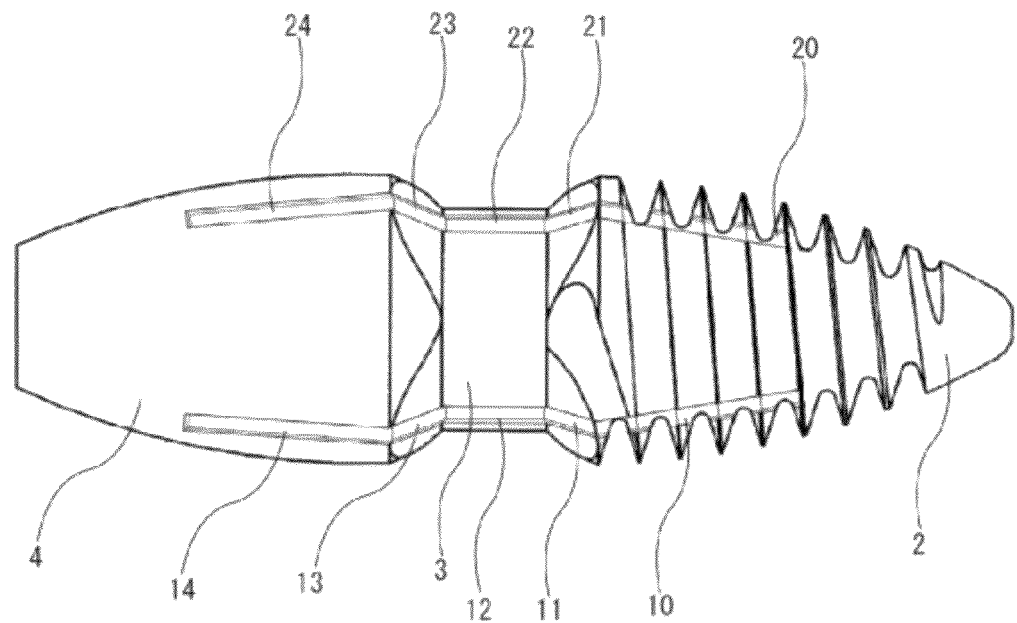
FIG. 7 shows a plane view of the interspinous implant.
Figure 8:
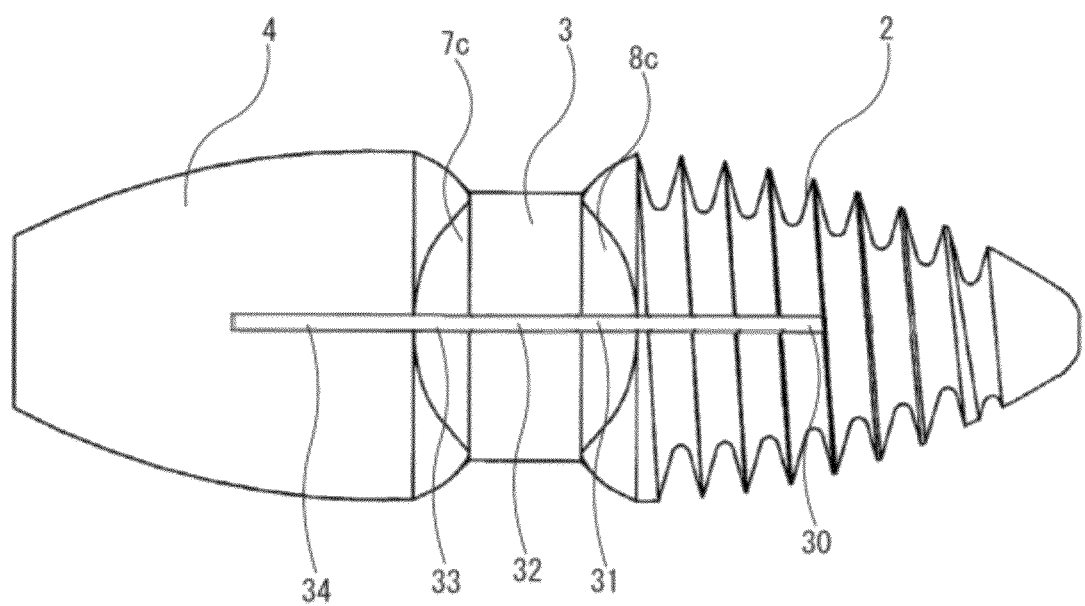
FIG. 8 shows a bottom surface view of the interspinous implant.

FIGS. 1 to 8 show a contour of the interspinous implant according to Embodiment 1. FIG. 1 is an external perspective view of the interspinous implant in Embodiment 1 to be seen from a screw region. FIG. 2 is an external perspective view of the present interspinous implant to be seen from a head region. FIG. 3 is a front view of the present interspinous implant (long axis direction is disposed horizontally). FIG. 4 is a right side view of the present interspinous implant (to be seen from the screw region toward the axis direction). FIG. 5 is a left side view of the present interspinous implant (to be seen from the head region toward the axis direction). FIG. 6 is a rear view of the present interspinous implant. FIG. 7 is a plane view of the present interspinous implant. FIG. 8 is a bottom surface view of the present interspinous implant.

The interspinous implant 1 in Embodiment 1 is as shown in FIGS. 1 to 8 and composed of a substantially conoid screw region 2, a head region 4 of a substantially inverse truncated conoid shape formed coaxially with the screw region, a spacer region 3 formed in an axial direction between the screw region 2 and the head region 4, a through-hole 5 penetrating an axial center of the screw region 2, the spacer region 3 and the head region 4, and three grooves (10 to 14, 20 to 24 and 30 to 34).

The grooves (10 to 14, 20 to 24 and 30 to 34) are formed continuously to cover half of a dimension of the substantially conoid shape of the screw region 2 in the axial direction, an entire axial direction of the spacer region 3 and half of a dimension of the substantially inverse truncated conoid shape of the head region 4 in the axial direction.

The screw region 2 of the present interspinous implant 1 has a substantially radial outer contour. This is because when the screw region 2 passes through a processus spinosus interspace, the processus spinosus interspace can be enlarged by the radial outer contour and the spacer region 3 is easily fitted in the processus spinosus interspace. Further, a cross section of the spacer region 3 in the interspinous implant 1 is formed into a substantially triangular shape.

Moreover, by including a hole 6 for a hexagon driver, the interspinous implant 1 in Embodiment 1 can be pushed from a small incision site toward an internal processus spinosus interspace by rotating the interspinous implant 1 using a driver tool.

The present interspinous implant 1 can also be coupled with a guide pin by including the through-hole 5 for guide pin insertion, and the guide pin is inserted from a small incision site toward an internal processus spinosus interspace so that the present interspinous implant 1 can be guided to the processus spinosus interspace along the guide pin.

Further, the interspinous implant 1 in Embodiment 1 includes the spacer region 3 which has been made by scraping away the center of an elliptical sphere made from titanium, and the screw region 2 which has been made by providing screw threads on a side surface in one end.

The tip end part of the screw region 2 has been formed into a conoid shape having a round tip, but this may be formed into a hemisphere. In addition, a joint of the screw region 2 and the spacer region 3 has been created by expanding an end-to-side of the spacer region 3 to a coronal side of the screw region 2 so as to be made adjacent without a step but may have a distinctive step.

Figure 9:
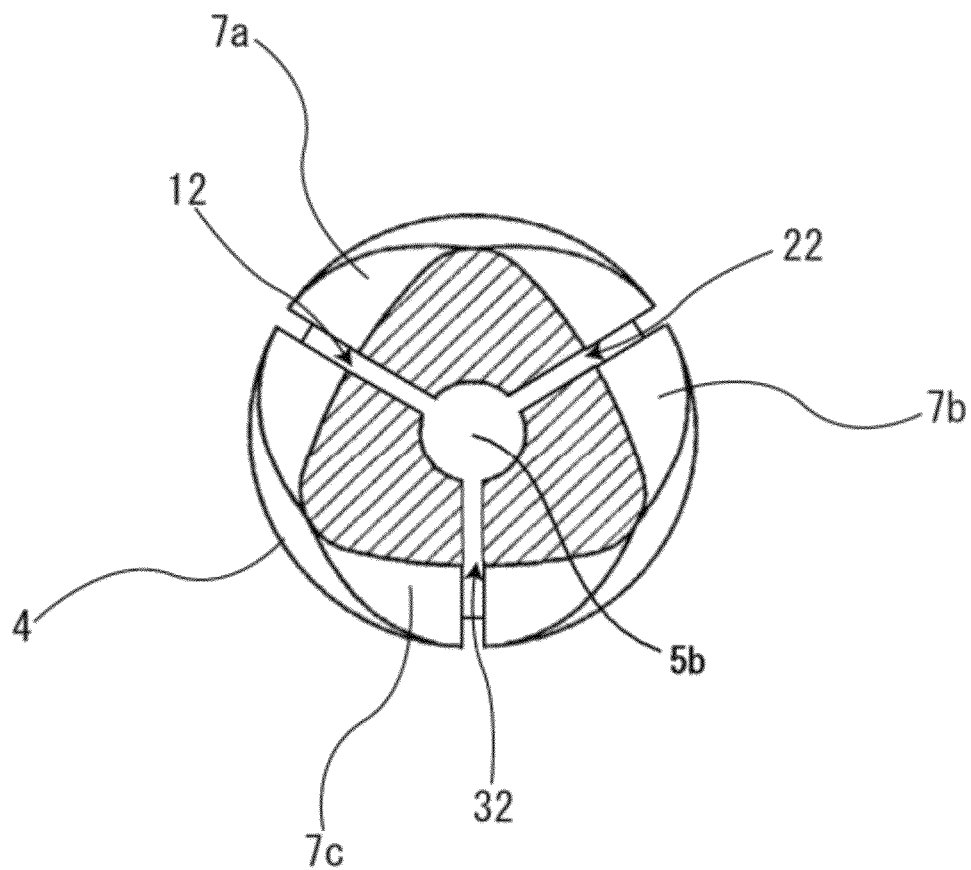
FIG. 9 shows a cross sectional view of the spacer region in the interspinous implant according to Embodiment 1 (cross sectional view of A-A').

FIG. 9 is a cross sectional view of the spacer region in the interspinous implant according to Embodiment 1 (cross sectional view of A-A' in FIG. 3). FIG. 9 shows a substantially triangular cross section of the spacer region 3. The grooves (12, 22 and 32) are created at the center of each three sides of the substantially triangular shape with a depth reaching a through hole 5b, respectively.

Figure 16:
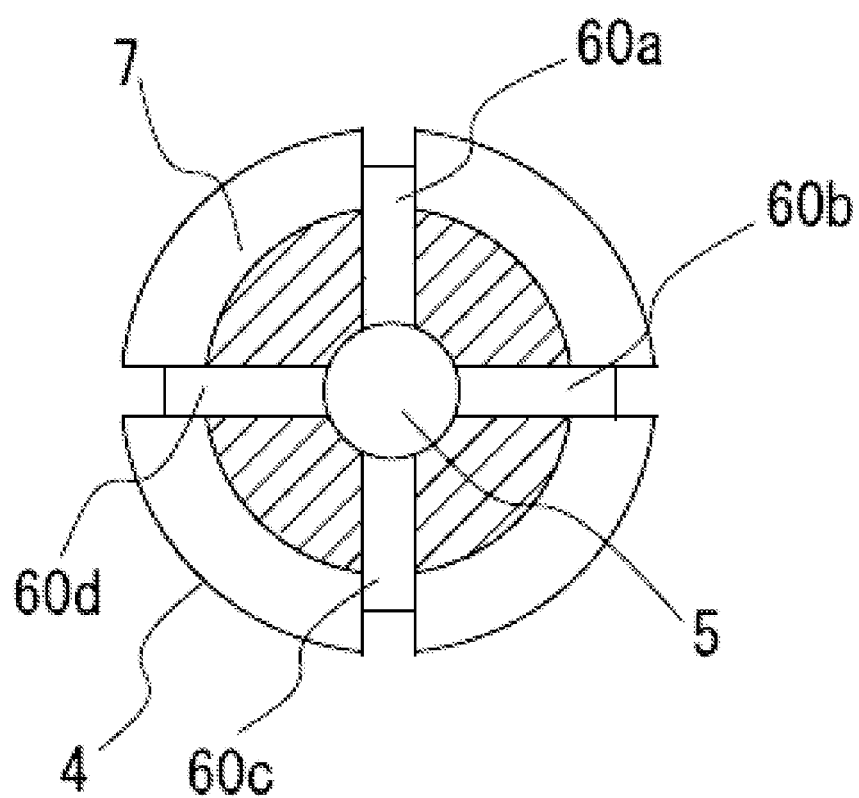
FIG. 16 shows a cross sectional view of the spacer region in the interspinous implant according to a modified second embodiment.

FIG. 16 is a cross sectional view of the spacer region in the interspinous implant according to a modified second embodiment. FIG. 16 shows a substantially circular cross section of the spacer region 3. Four grooves (60a, 60b, 60c, 60d), with a depth reaching a through hole 5, are arranged at 90° intervals to be seen from the axial direction.

Figure 17:
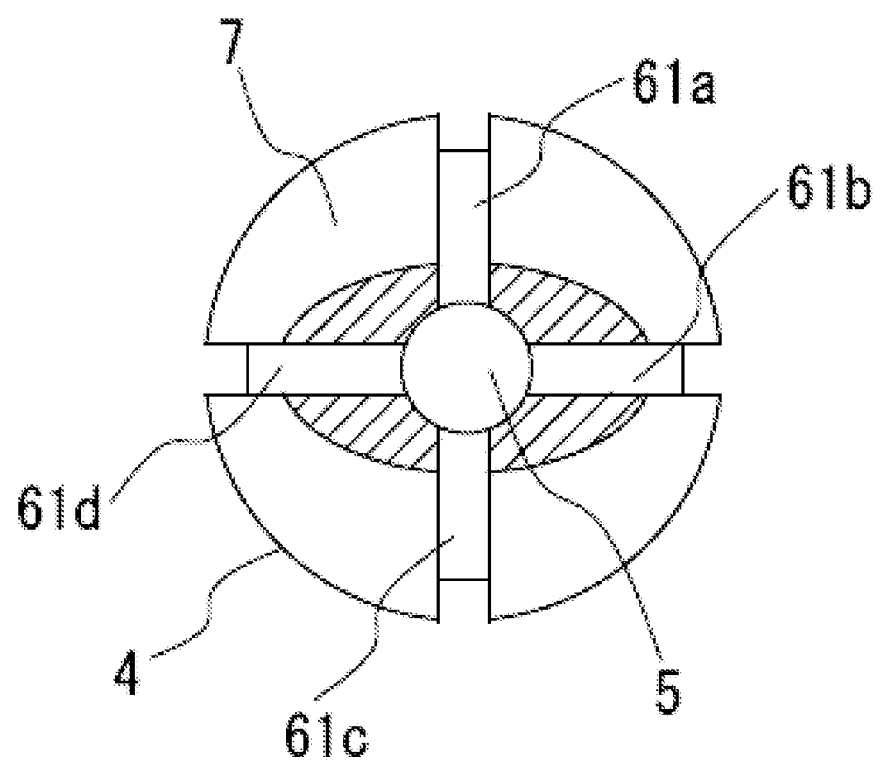
FIG. 17 shows a cross sectional view of the spacer region in the interspinous implant according to a modified third embodiment.

FIG. 17 is a cross sectional view of the spacer region in the interspinous implant according to a modified third embodiment. FIG. 17 shows a substantially elliptical cross section of the spacer region 3. Four grooves (61a, 61b, 61c, 61d), with a depth reaching a through hole 5, are arranged at 90° intervals to be seen from the axial direction.

It should be noted that although FIGS. 16 and 17 show four grooves that are arranged at 90° intervals to be seen from the axial direction, another modification would include only three slits or grooves arranged at 120° intervals to be seen from the axial direction.

Figure 18:
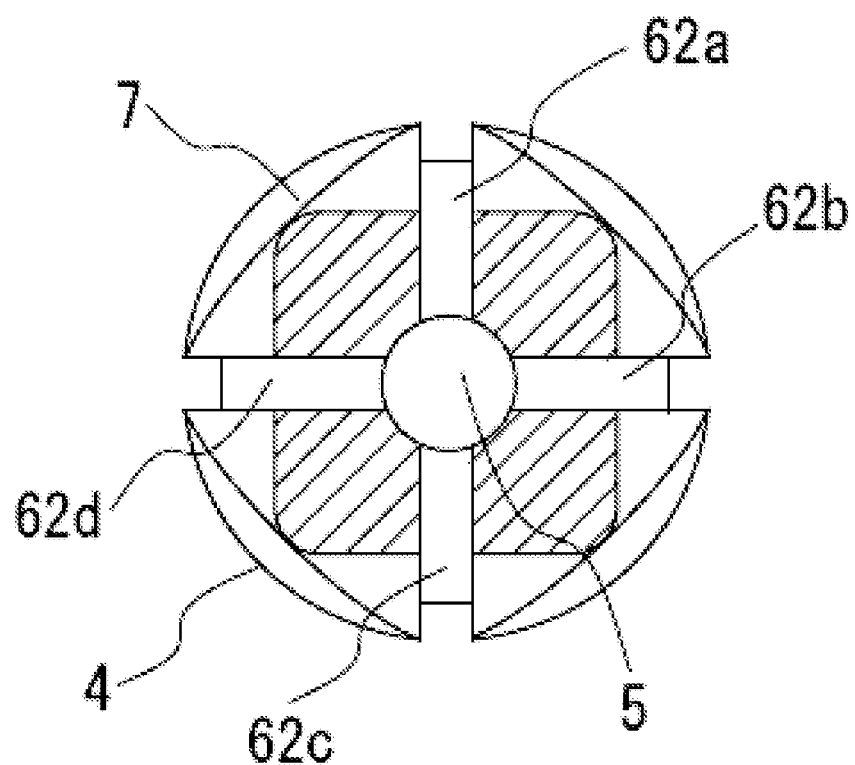
FIG. 18 shows a cross sectional view of the spacer region in the interspinous implant according to a modified fourth embodiment.

FIG. 18 is a cross sectional view of the spacer region in the interspinous implant according to a modified fourth embodiment. FIG. 18 shows a substantially rectangular cross section of the spacer region 3. Four grooves (62a, 62b, 62c, 62d), with a depth reaching a through hole 5, are arranged at 90° intervals to be seen from the axial direction. The four grooves (62a, 62b, 62c, 62d) are respectively arranged in the vicinity of the center of the four flat side surfaces of the rectangularly shaped spacer region 3.

Figure 10:
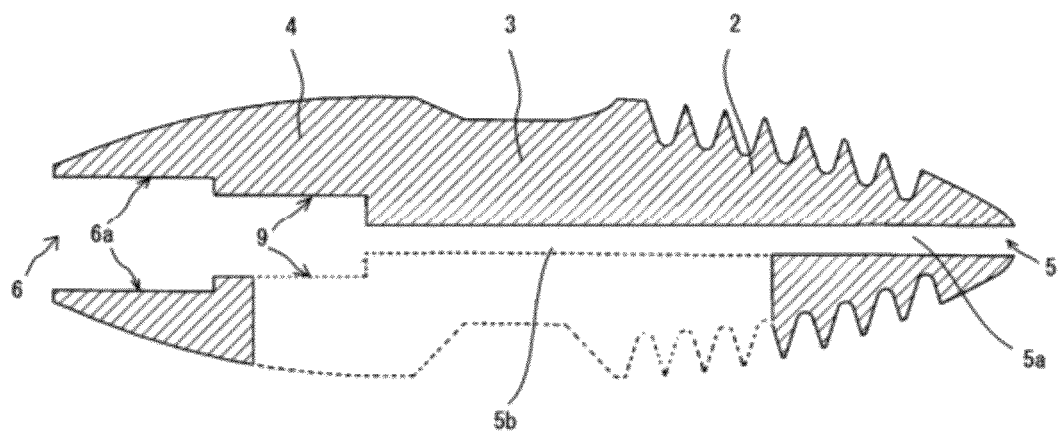
FIG. 10 shows a cross sectional view of the entire shape of the interspinous implant according to Embodiment 1 (cross sectional view of B-B').

Also shown in FIG. 10 is a cross sectional view of the entire shape of the interspinous implant according to Embodiment 1 (cross sectional view of B-B' in FIG. 5). The shape is not vertically symmetrical relative to the long axis in FIG. 10 because it is affected by the grooves (30 to 34) provided downward with a depth reaching the through-hole 5b in a lower side.

The through-hole continued from the through-hole 5 inside the implant has a small inner diameter (5a) in the vicinity of an inlet of the screw region 2 but has a large inner diameter (5b) inside the implant (from the screw region 2 to the spacer region 3). The head region 4 also internally contains an inner wall part (6a) which is continued from the hole 6 for hexagonal driver and can be engaged with a hexagonal driver, and a thread cut 9 into which a tool with screw threads can be screwed.

Figure 11:
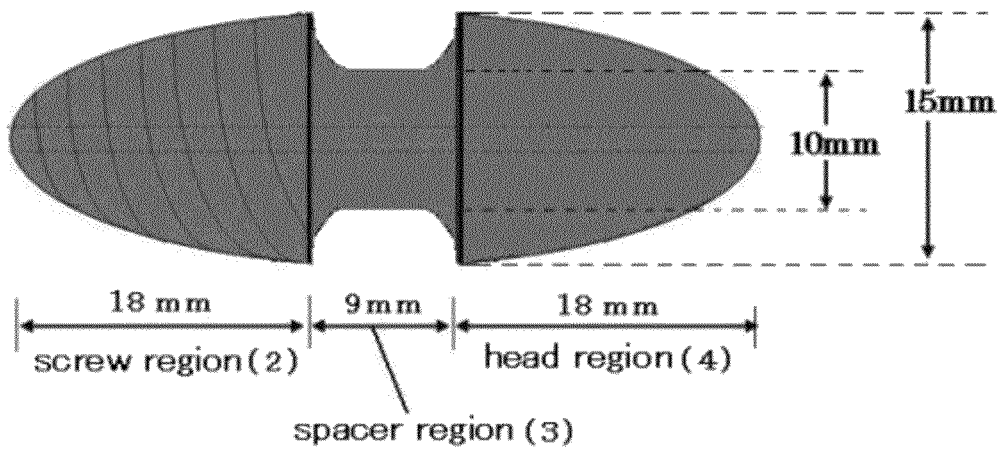
FIG. 11 shows a view of dimensions of the entire shape of the interspinous implant according to Embodiment 1.

FIG. 11 shows one example of a dimension of the entire shape of the interspinous implant according to Embodiment 1.

A full length of the screw region 2 is 18 mm in the axial direction, a full length of the spacer region 3 is 9 mm in the axial direction and a full length of the head region 4 is 18 mm in the axial direction. Regarding a dimension of the substantially triangular cross section of the spacer region 3, a diameter of the circle circumscribing vertexes of the triangle is 10 mm. A diameter of the edge of the conoid shape is 15 mm in the screw region 2 and the head region 4. Here, a pitch of screw threads in the screw region 2 is about 1 mm and the screw threads are produced so as to protrude from the radial outer contour of the screw region 2. The through-hole also has a diameter of about 1 to 2 mm. Each of the grooves also has a width of about 1 mm and a depth reaching the through-hole, or more precisely the depth is set to about a radius (5 to 7 mm) of the conoid shape in the screw region 2, about 4 mm in the spacer region 3 and about a radius (5 to 7 mm) of the conoid shape in the head region 4.

Note that multiple variations can be applied to the dimension (length and diameter) of the screw region 2, the spacer region 3 and the head region 4 depending on the condition of a processus spinosus interspace in a diseased part.

When the screw region 2 of the interspinous implant 1 is passed through processus spinosus 10, the spacer region 3 of the interspinous implant 1 is pinched, and the processus spinosus interspace can be stably enlarged and fixed.

Figure 12:
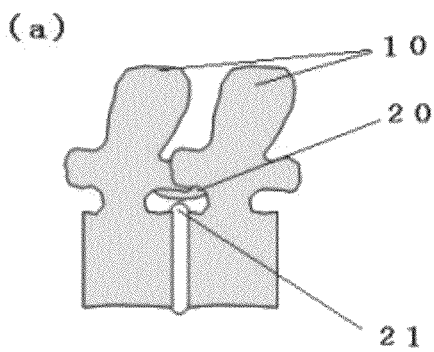
FIG. 12 shows an explanatory diagram of the use the interspinous implant according to Embodiment 1.
Figure 12:
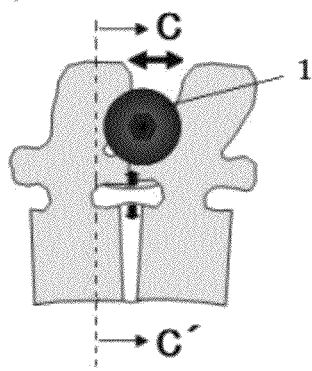
Figure 12:
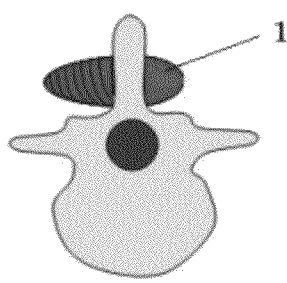

FIG. 12 shows how the interspinous implant according to Embodiment 1 is used. FIG. 12a is a side cross sectional view of spinal canal and FIGS. 12b and 12c show the appearance where the interspinous implant 1 according to Embodiment 1 has been fitted in the spinal canal. Here, 10 represents processus spinosus, 20 represents a hypertrophic yellow ligament and 21 represents the swelling of intervertebral disc. It can be seen that the spinal canal is stenosed in FIG. 12a and as shown in FIG. 12b, the spinal canal has been enlarged by the interspinous implant 1 according to Embodiment 1.

Explained next will be a tap for interspinous implant by referring to FIGS. 13 to 14.

Figure 13:
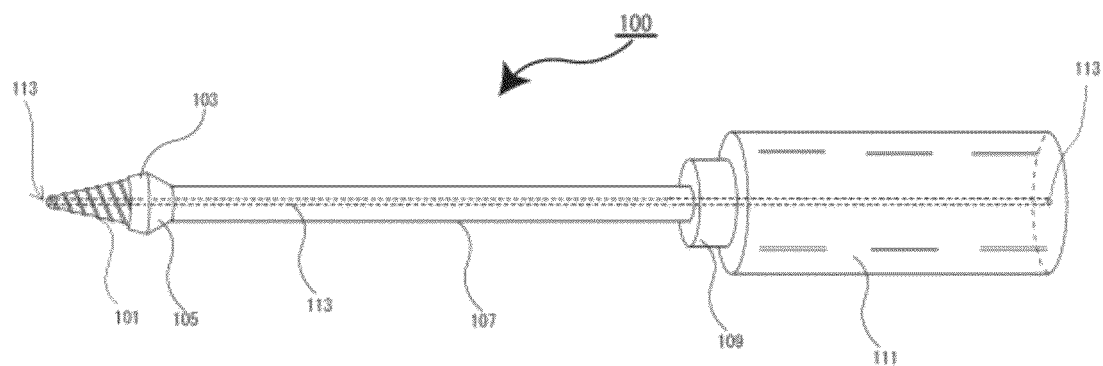
FIG. 13 shows an explanatory diagram of a tap for interspinous implant.
Figure 14:
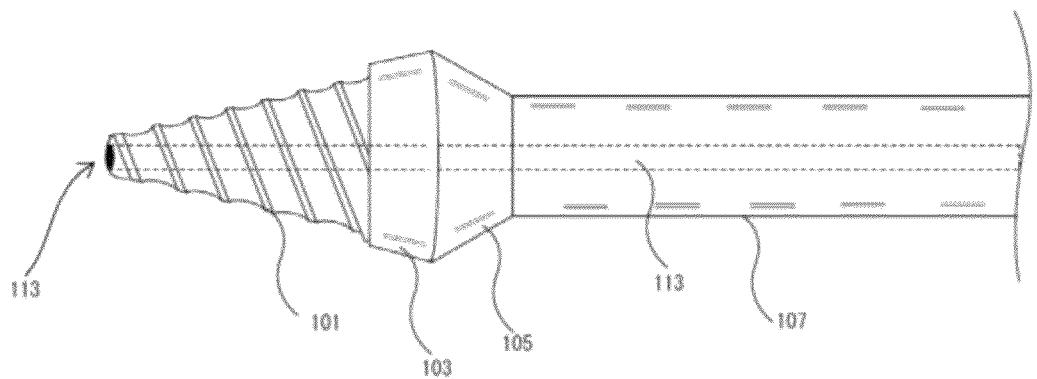
FIG. 14 shows an enlarged view of the tip of the tap for interspinous implant.

The tap for interspinous implant is as shown in FIGS. 13 and 14 and composed of a tip end region 101 which is formed into a conoid shape with a more acute angle than the conus of the screw region of the interspinous implant and provided with screw threads occupying one fifth of the generatrix from the tip end of the conoid shape, an axial center region 107 extending in an axial direction of the tip end region 101, whose diameter is less than a diameter of skirts 103 of the tip end region 101 and whose dimension in a longitudinal direction exceeds a length from an incision site to a processus spinosus, a grip region 111 fitted in the axial center region 107, and a through-hole 113 linearly penetrating a space from the tip end region 101 to the end of the grip region 111 by passing through the axial center region 107.

The skirts 103 of the tip end region 101 and the axial center region 107 are joined to form a taper without producing a step. Owing to the gentle shape without a step, the present tap can be inserted and extracted smoothly.

In addition, bypassing a guide pin not shown through the through-hole 113 which linearly penetrates a space from the tip end region 101 to the end of the grip region 111 by passing through the axial center region 107 of the tap for interspinous implant, the tap can be inserted into the body along the guide pin.

Figure 15:
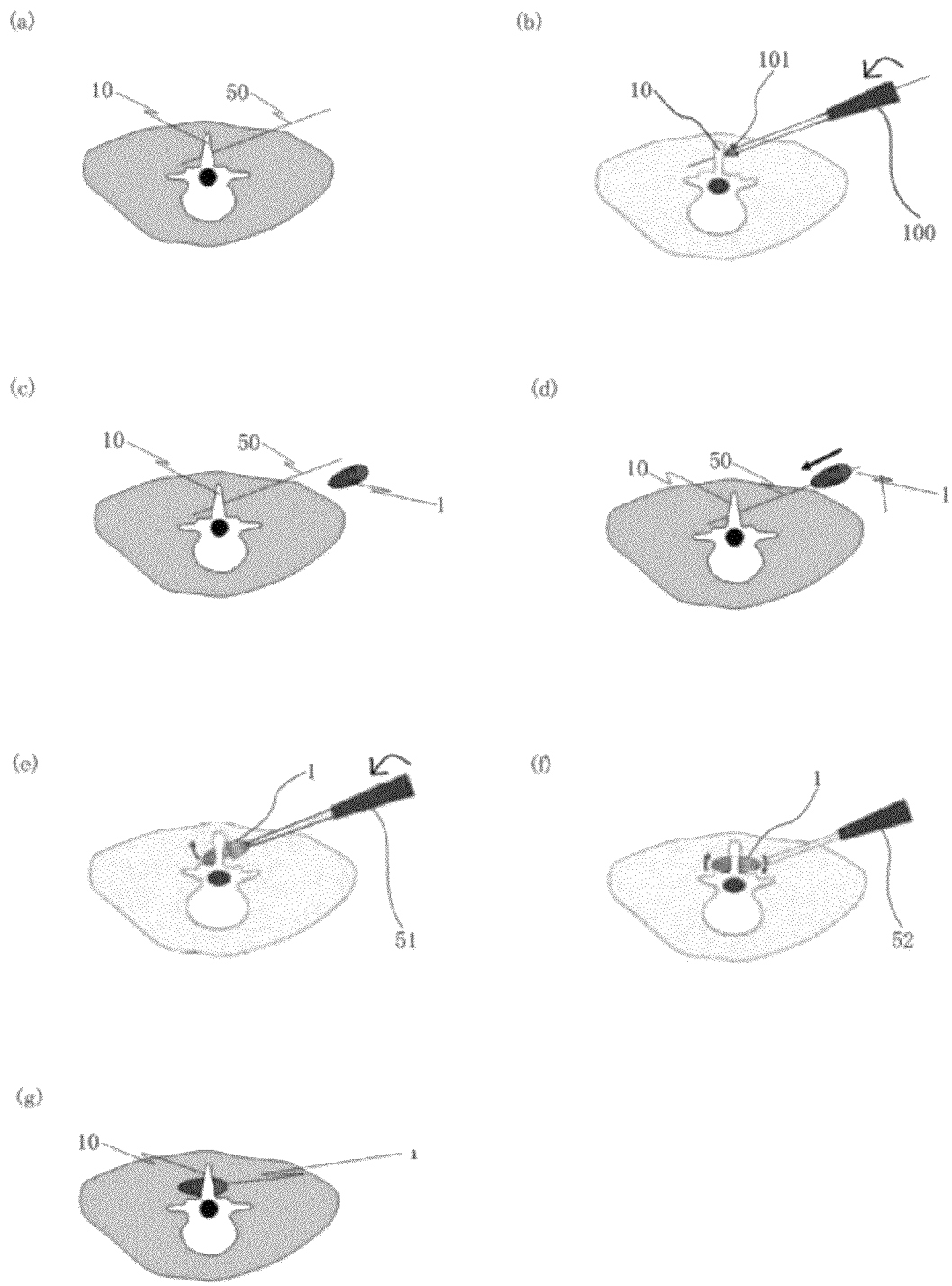
FIG. 15 shows an explanatory diagram of the insertion procedure of the interspinous implant.

Next, an insertion procedure protocol of the present interspinous implant and the present tap for interspinous implant will be described by the following procedures a) to j). Also shown in FIG. 15 is an explanatory diagram of the insertion procedure of the present interspinous implant.

a) Radioscopy (image) is performed on a knee/chest position. A distance of a processus spinosus interspace is measured to determine a full length of the interspinous implant in the axial direction and a width of the spacer region. Also, an entry point and an angle of the guide pin are measured on a CT image.

b) The entry point of the guide pin is determined according to the measurement. A horizontal incision of about 2 cm is made on the skin at the determined position in order to insert a guide pin 50 (see FIG. 15a). It is confirmed under radioscopy (image) that the guide pin 50 has passed a portion as close as possible to the base of the target processus spinosus interspace and the tip end of the guide pin 50 has passed over an opposed intervertebral joint.

c) From the horizontal skin incision position of about 1 cm, the tap 100 for interspinous implant is inserted and a passage is created in the processus spinosus interspace to some extent by using the tip end region 101 of the tap so as to slightly open and enlarge an interval of the processus spinosus 10 (see FIG. 15b).

d) The tap 100 for interspinous implant is removed. The guide pin 50 remains inserted (see FIG. 15c).

e) By passing the guide pin 50 through the through-hole of the interspinous implant 1, the interspinous implant 1 is inserted into the body (see FIG. 15d).

f) The interspinous implant 1 is allowed to proceed using a hexagonal driver 51.

g) When the tip end part of the screw region of the interspinous implant 1 reaches the processus spinosus interspace, the implant is inserted by adding a rotational force to the hexagonal driver 51 (see FIG. 15e). The screw region proceeds by opening and enlarging the processus spinosus interspace. The spacer region is pinched, thereby the interspinous implant 1 is fixed.

h) The hexagonal driver 51 is changed to a multi-axial driver 52 (having a paper-covered lamp shape in a tip end) and the guide pin 50 is removed, followed by adjusting a position (slope) of the interspinous implant 1 (see FIG. 15f).

i) The position of the interspinous implant 1 is confirmed again by radioscopy (image), and subsequently the multi-axial driver 52 is removed (see FIG. 15g).

(j) The fascias and skin are sewn to finish the operation.

The interspinous implant and the tap for interspinous implant according to the present invention are as explained above. Application of the interspinous implant according to the present invention is not limited to stenosis and it is possible to consider other applications. For example, in a case such as lumbar pain caused by instability of a space between adjacent vertebrae, vertebrae interspace can be stabilized to some extent by inserting the interspinous implant according to the present invention and therefore effects of reducing symptoms can be anticipated.

Industrial Applicability

The interspinous process spacer according to the present invention is anticipated to be utilized as a medical device useful for surgical therapy of spinal canal stenosis.

What is claimed is:

1. An interspinous implant for maintaining a predetermined interval between adjacent processus spinosus, the implant comprising:
   a substantially conoid screw region having screw threads being screwable into a processus spinosus interspace;
   a head region of a substantially inverse truncated conoid shape formed coaxially with the screw region;
   a spacer region formed in an axial direction between the screw region and the head region; and
   a through-hole penetrating an axial center of the screw region, the spacer region, and the head region, wherein
   a plurality of slits or grooves is formed in an axial direction of the entire shape of the implant, the plurality of slits or grooves occupying more than one third of the full length of the implant in the axial direction,
   each of the plurality of slits or grooves is deep enough to reach the through hole,
   the plurality of the slits or grooves is arranged in the implant at even intervals,
   each of the plurality of slits or grooves is formed continuously in the axial direction through the screw region, the spacer region, and the head region, and
   neither end of each of the plurality of slits or grooves is formed so as to extend to an open end of the screw region or an open end of the head region.

2. The interspinous implant according to claim 1, wherein each of the plurality of slits or grooves is formed continuously to cover more than half of a dimension of the substantially conoid shape of the screw region in the axial direction, a whole dimension of the spacer region in the axial direction, and more than a half of a dimension of the substantially inverse truncated conoid shape of the head region in the axial direction.

3. The interspinous implant according to claim 1, wherein a width of each of the plurality of slits or grooves falls in a range of 0.5 to 1.5 mm.

4. The interspinous implant according to claim 1, wherein the entire shape of the implant is a spindle shape.

5. The interspinous implant according to claim 1, wherein a cross section of the spacer region is circular, elliptical, substantially triangular, substantially rectangular or polygonal with the plurality of the slits or grooves arranged in the cross section of the spacer region at even intervals.

6. The interspinous implant according to claim 1, wherein
a cross section of the spacer region is circular or elliptical, and
three slits or grooves are arranged at 120° intervals to be seen from the axial direction, or four slits or grooves are arranged at 90° intervals to be seen from the axial direction.

7. The interspinous implant according to claim 1, wherein
a cross section of the spacer region is substantially triangular, and
three slits or grooves are arranged in the vicinity of the center of three flat side surfaces.

8. The interspinous implant according to claim 1, wherein
a cross section of the spacer region is substantially rectangular, and
four slits or grooves are arranged in the vicinity of the center of four flat side surfaces.

\* \* \* \* \*